United States Patent
Koontz et al.

(10) Patent No.: US 12,167,980 B2
(45) Date of Patent: Dec. 17, 2024

(54) INTRAOCULAR DEVICE FOR DUAL INCISIONS

(71) Applicant: NEW WORLD MEDICAL, INC., Rancho Cucamonga, CA (US)

(72) Inventors: John Koontz, Chino, CA (US); Eric Porteous, Corona, CA (US)

(73) Assignee: NEW WORLD MEDICAL, INC., Rancho Cucamonga, CA (US)

( * ) Notice: Subject to any disclaimer, the term of this patent is extended or adjusted under 35 U.S.C. 154(b) by 939 days.

(21) Appl. No.: 17/274,077

(22) PCT Filed: Sep. 20, 2019

(86) PCT No.: PCT/US2019/052260
§ 371 (c)(1),
(2) Date: Mar. 5, 2021

(87) PCT Pub. No.: WO2020/068595
PCT Pub. Date: Apr. 2, 2020

(65) Prior Publication Data
US 2021/0212859 A1 Jul. 15, 2021

Related U.S. Application Data

(60) Provisional application No. 62/735,760, filed on Sep. 24, 2018.

(51) Int. Cl.
*A61F 9/007* (2006.01)
(52) U.S. Cl.
CPC ................ *A61F 9/00781* (2013.01)

(58) Field of Classification Search
CPC ............. A61F 9/00736; A61F 9/00754; A61F 9/00781; A61F 9/0133; A61B 17/32093; A61B 17/3211; A61B 2017/32113
See application file for complete search history.

(56) References Cited

U.S. PATENT DOCUMENTS

| 2006/0015128 A1 | 1/2006 | Fard |
| 2016/0354248 A1* | 12/2016 | Kahook ............... A61F 9/00781 |
| 2017/0181892 A1* | 6/2017 | Kahook ................ A61F 9/0133 |

FOREIGN PATENT DOCUMENTS

| WO | WO-2013163034 A1 | 10/2013 |
| WO | WO-2017112893 A1 | 6/2017 |
| WO | WO-2018151808 A1 | 8/2018 |

OTHER PUBLICATIONS

Extended European Search Report for Application No. 19864476.7, dated May 23, 2022, 7 pages.
International Search Report and Written Opinion for Application No. PCT/US2019/052260, dated Dec. 5, 2019, 13 pages.

* cited by examiner

*Primary Examiner* — Todd J Scherbel
(74) *Attorney, Agent, or Firm* — MORGAN, LEWIS & BOCKIUS LLP

(57) ABSTRACT

An ophthalmic device and methods of its use can be applied for treatment of various conditions including eye diseases, such as glaucoma, using minimally invasive surgical techniques. The ophthalmic device can be used to cut the trabecular meshwork (TM) in the eye. The device tip provides entry into the Schlemm's canal and ramped portions elevate the TM under tension and guide it to lateral blades. An entire strip of TM can be removed without leaving TM leaflets behind and without causing collateral damage to adjacent tissues.

20 Claims, 10 Drawing Sheets

INTRAOCULAR DEVICE FOR DUAL INCISIONS

CROSS-REFERENCE TO RELATED APPLICATIONS

This application is the national stage of International Patent Application No. PCT/US2019/052260, entitled "INTRAOCULAR DEVICE FOR DUAL INCISIONS," filed Sep. 20, 2019, which claims the benefit of U.S. Provisional Application No. 62/735,760, entitled "INTRAOCULAR DEVICE FOR DUAL INCISIONS," filed Sep. 24, 2018, the entirety of which are incorporated herein by reference.

BACKGROUND

There are numerous medical and surgical procedures in which it is desirable to cut and remove a strip of tissue of controlled width from the body of a human or veterinary patient. For example, it may sometimes be desirable to form an incision of a controlled width (e.g., an incision that is wider than an incision made by a typical scalpel, cutting blade or needle) in the eye, skin, mucous membrane, tumor, organ or other tissue or a human or animal. In addition, it may sometimes be desirable to remove a strip or quantity of tissue from the body of a human or animal for use as a biopsy specimen, for chemical/biological analysis, for retention or archival of DNA identification purposes, etc. In addition, some surgical procedures require removal of a strip of tissue of a known width from an anatomical location within the body of a patient.

One surgical procedure wherein a strip of tissue of a known width is removed from an anatomical location within the body of a patient is an ophthalmological procedure used to treat glaucoma. This ophthalmological procedure is sometimes referred to as a goniotomy. In a goniotomy procedure, a device that is operative to cut or ablate a strip of tissue of approximately 2-10 mm in length or more and about 50-230 μm in width is inserted into the anterior chamber of the eye and used to remove a full thickness strip of tissue from the trabecular meshwork. The trabecular meshwork is a loosely organized, porous network of tissue that overlies a collecting canal known as Schlemm's canal. A fluid, known as aqueous humor, is continually produced in the anterior chamber of the eye. In healthy individuals, aqueous humor flows through the trabecular meshwork, into Schlemm's canal and out of the eye through a series of ducts called collector channels. In patients who suffer from glaucoma, the drainage of aqueous humor from the eye may be impaired by elevated flow resistance through the trabecular meshwork, thereby resulting in an Increase in intraocular pressure. The goniotomy procedure can restore normal drainage of aqueous humor from the eye by removing a full thickness segment of the trabecular meshwork, thus allowing the aqueous humor to drain through the open area from which the strip of trabecular meshwork has been removed.

SUMMARY

Embodiments of the present disclosure can be used for surgical medicinal intervention. For example, some embodiments relate to a microsurgical device and methods of its use for treatment of various medical conditions including but not limited to eye diseases, such as glaucoma, using minimally invasive surgical techniques. Specifically, the device may be a dual-blade device for cutting the trabecular meshwork ("TM") in the eye. In particular, the device may have a device tip providing entry into the Schlemm's canal via its size (i.e., for example, between approximately 0.2-0.3 mm width) and a configuration where the entry blade tip ramps upwardly providing a wedge or ramp-like action for cutting the TM.

To facilitate the understanding of the present disclosure, a number of terms are defined below.

Terms defined herein have meanings as commonly understood by a person of ordinary skill in the areas relevant to the present disclosure. Terms such as "a," "an," and "the" are not intended to refer to only a singular entity, but include the general class of which a specific example may be used for illustration.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

The term "therapeutically effective amounts" or "pharmaceutically effective amounts", as used herein means that amount which, when administered to a subject or patient for treating a disease, is sufficient to effect such treatment for the disease or to ameliorate one or more symptoms of a disease or condition (e.g. ameliorate pain).

As used herein, the terms "treat" and "treating" are not limited to the case where the subject (e.g. patient) is cured and the disease is eradicated. Rather, embodiments of the present disclosure also contemplate treatment that merely reduces symptoms, improves (to some degree) and/or delays disease progression. It is not intended that embodiments of the present disclosure be limited to instances wherein a disease or affliction is cured. It is sufficient that symptoms are reduced.

As used herein "goniotomy" refers to a surgical procedure primarily used to treat various types of glaucoma (ex, primary open angle glaucoma).

As used herein "trabecular meshwork" refers to area of tissue in the eye located around the base of the cornea, near the ciliary body, (between the scleral spur and Schwalbe's line) and is responsible for draining the aqueous humor from the eye via the anterior chamber (the chamber on the front of the eye covered by the cornea). The tissue is spongy and lined by trabeculocytes; it allows fluid to drain into a circular channel in the eye called Schlemm's canal and eventually flowing into the blood system.

As used herein "Schlemm's canal" refers to a circular channel in the eye that collects aqueous humor from the anterior chamber and delivers it into the bloodstream via the collector channels and anterior ciliary veins.

As used herein "eye diseases" refers to various conditions of the eye including, but not limited to Glaucoma—optic neuropathy, Glaucoma suspect—ocular hypertension, Primary open-angle glaucoma, Primary angle-closure glaucoma, primary open angle glaucoma, normal or low tension glaucoma, pseudoexfoliation glaucoma, pigment dispersion glaucoma, angle closure glaucoma (acute, subacute, chronic), neovascular or inflammatory glaucoma, ocular hypertension, and other types of glaucoma that are related to dysregulation of intraocular pressure.

As used herein "hypotony" refers to reduced intraocular pressure. The statistical definition of hypotony is intraocular pressure ("TOP") less than 6.5 mm Hg, which is more than 3 standard deviations below the mean TOP. The clinical definition of hypotony is TOP low enough to result in pathology (vision loss). The vision loss from low TOP may be caused by corneal edema, astigmatism, cystoid macular edema, maculopathy, or other condition. Hypotony maculopathy is characterized by a low TOP associated with fundus abnormalities, including chorioretinal folds, optic nerve head edema in the acute setting, and vascular tortuosity.

As used herein "Schwalbe's line" refers to the anatomical line found on the interior surface of the eye's cornea, and delineates the outer limit of the corneal endothelium layer. Specifically, it represents the termination of Descemet's membrane.

As used herein "Descemet's membrane" refers to the basement membrane that lies between the corneal proper substance, also called stroma, and the endothelial layer of the cornea.

As used herein "scleral spur" refers to an annular structure composed of collagen in the human eye, a protrusion of the sclera into the anterior chamber. It is the origin of the longitudinal fibers of the ciliary muscle and is attached anteriorly to the trabecular meshwork. Open-angle glaucoma (OAG) and closed-angle glaucoma (CAG) may be treated by muscarinic receptor agonists (e.g., pilocarpine), which cause rapid miosis and contraction of the ciliary muscles, this pulls the scleral spur and results in the trabecular meshwork being stretched and separated. This opens the fluid pathways and facilitates drainage of the aqueous humour into the canal of Schlemm and ultimately decreasing intraocular pressure.

Embodiments of the present disclosure are illustrated, for example, according to various aspects described below.

Devices disclosed herein can be used for incising a trabecular meshwork, including the steps of: providing a device for incising the trabecular meshwork, the device comprising: a platform for elevating a portion of the trabecular meshwork away from an outer wall of a Schlemm's canal, the platform comprising a tip at a distal side of the platform and a ramp extending from the distal side to a proximal side of the platform, opposite the distal side of the platform, wherein the ramp increases from a distal thickness at the distal side to a proximal thickness, greater than the distal thickness, at the proximal side; and first and second lateral elements for creating first and second incisions through the trabecular meshwork; inserting the tip into a Schlemm's canal of a patient; advancing the ramp between the trabecular meshwork and an outer wall of the Schlemm's canal such that (i) a portion of the trabecular meshwork is elevated away from the outer wall of the Schlemm's canal, (ii) the portion remains attached to adjacent portions of the trabecular meshwork on opposing sides of the ramp, and (iii) the portion is guided to the first and second lateral elements; and creating first and second incisions through the trabecular meshwork with each of the first and second lateral elements while the trabecular meshwork is elevated away from the outer wall of the Schlemm's canal so a strip of the trabecular meshwork has a width between the first and second incisions corresponding to the width of the gap.

Creating the first and second incisions can comprise creating only the first and second incisions. The strip between the first and second incisions remains intact after creating the first and second incisions. The method can further comprise excising the strip from the trabecular meshwork after the strip has reached a desired length. The excising can be performed with forceps. Creating the first and second incisions can be performed without ablation or burning of the trabecular meshwork. Creating the first and second incisions can be performed while the portion of the trabecular meshwork is stretched to be elevated away from the outer wall of the Schlemm's canal. Creating the first and second incisions can be performed while the portion of the trabecular meshwork is under tension that is greater than the tension of the trabecular meshwork in a natural state. The method can further comprise, while creating the first and second incisions, a portion of the strip is received within the gap. The first lateral element can create the first incision along a first portion of the trabecular meshwork that is guided along a first side of the platform, and the second lateral element can create the second incision along a second portion of the trabecular meshwork that is guided along a second side of the platform.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

DETAILED DESCRIPTION

Figure 1:
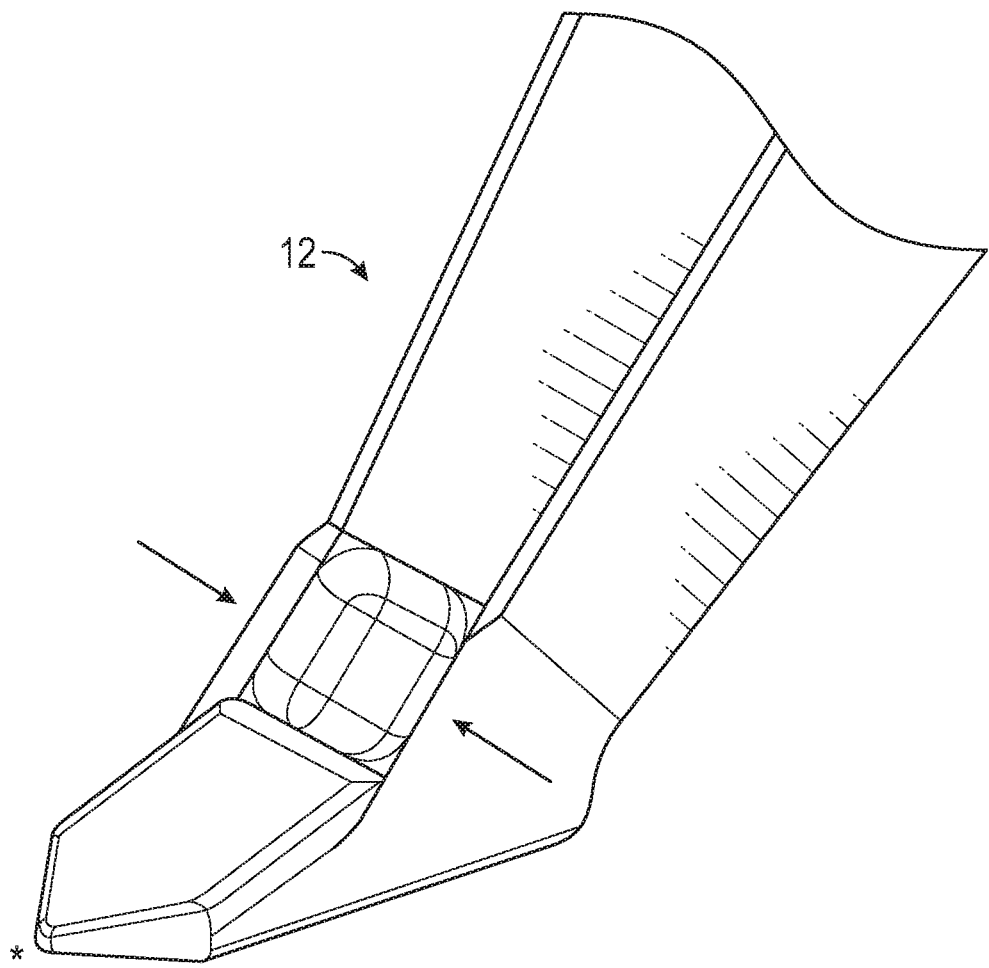
FIG. 1 shows a perspective view of an operative end of a dual blade device for treatment of glaucoma, according to some embodiments of the present disclosure.
Figure 2:
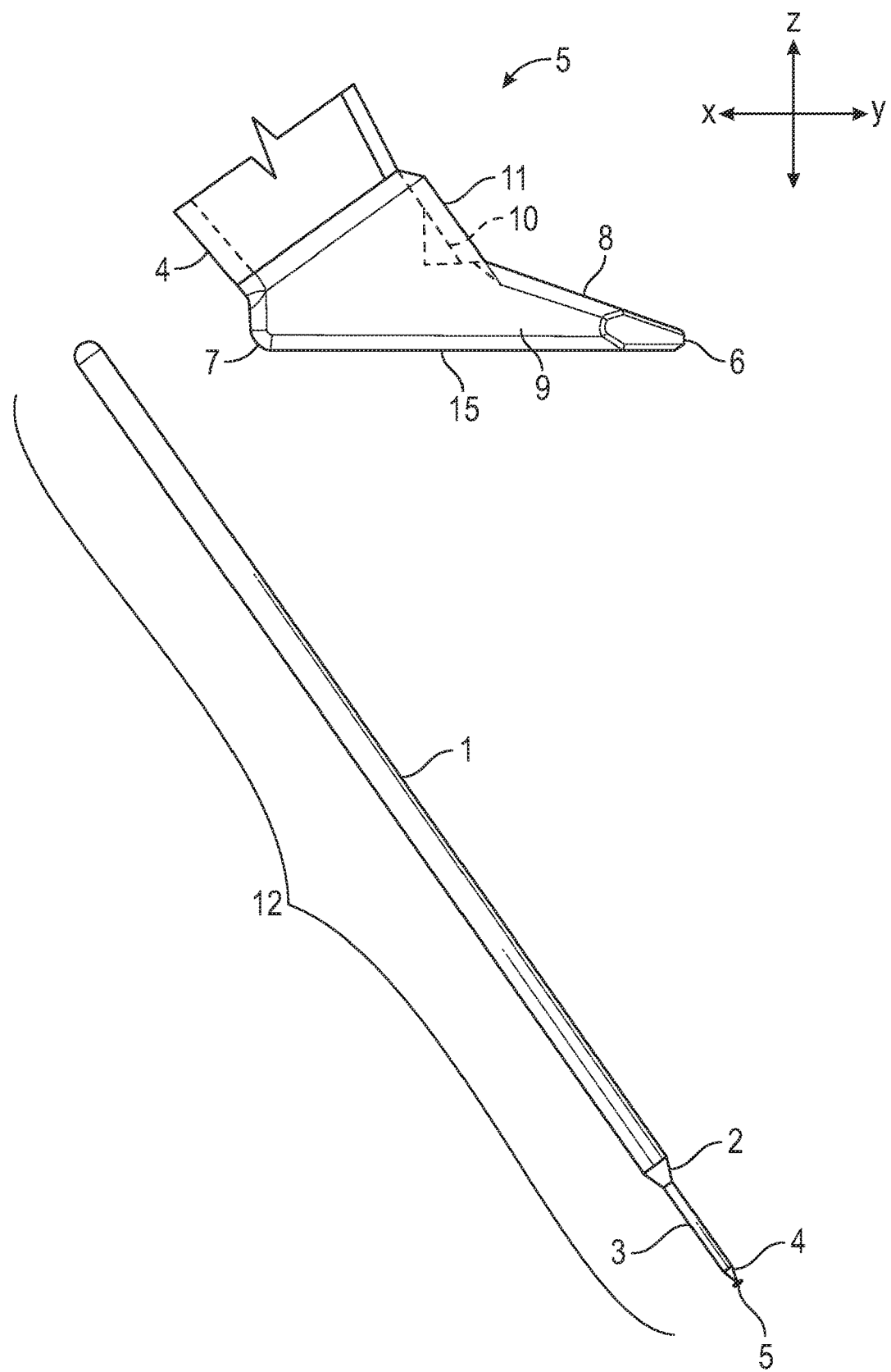
FIG. 2 shows a side view of a device with an enlarged detailed view of the operative end of the device.

In the following detailed description, specific details are set forth to provide an understanding of the subject technology. It will be apparent, however, to one ordinarily skilled in the art that the subject technology may be practiced without some of these specific details. In other instances, well-known structures and techniques have not been shown in detail so as not to obscure the subject technology.

There are several practical advantages of a dual blade device, as contemplated herein, for use in goniotomy. First, a dual blade device may be reusable and can be added to a standard cataract surgical tray. Second, the lack of moving parts or the need for coupled irrigation or a separate power source allows for inexpensive manufacturing and rapid acquisition of surgical expertise. This would permit easy, economical access to a new technique, especially in underserved locations around the world. The simple design and material requirements of dual-blade device embodiments would be more economical. Finally, in contrast to other techniques for TM removal, embodiments of dual-blade device designs conform to the Schlemm's canal anatomy, minimize damage to adjacent tissues, and provide excellent control over excised tissue. Therefore, the presented dual-blade minimally invasive glaucoma surgery ("MIGS") device represents a novel technique to perform a goniotomy with or without concomitant cataract extraction. In some embodiments, the dual-blade devices are capable of a more complete removal of TM tissue from the anterior chamber angle in a simple and inexpensive manner as compared to conventional devices. Perfusion eye studies support the potential for significant IOP reduction with this technique.

Glaucoma is believed to be one of the leading causes of blindness worldwide. It has been reported that a modifiable disease risk factor is intraocular pressure ("TOP"). Conventional treatment has centered on lowering IOP pharmaceutically with hypotensive medications or surgically through the use of lasers or incisional procedures. The main area of obstruction to aqueous outflow, with subsequent dysregulation of IOP, is thought to be located at the juxtacanalicular trabecular meshwork ("TM") and distal outflow structures. Performing a goniotomy or trabeculotomy in adults with glaucoma has not been associated with great success in lowering IOP. In contrast, these procedures have been reported to be more successful in congenital glaucoma, where a membrane covering the TM is thought to be a major factor in impedance of aqueous outflow. More recently, there have been attempts to use ab interno trabeculectomy procedures to remove TM in adult patients and results have been mixed.

One reason for poor long-term outcomes with this approach in adults might be related to incomplete removal of TM and membrane formation across the remaining TM leaflets with subsequent elevation in IOP. The dual-blade device is specifically designed to conform to the drainage angle anatomy of the human eye. The device can be used to perform a dual incision goniotomy by engaging TM and cutting the target tissue while minimizing leaflets left in place and damage to adjacent tissues.

Recently, there has been a growing trend toward innovations in MIGS. The risks and imperfections of guarded filtration surgery and tube shunt procedures have driven this paradigm shift despite the proven long-term efficacy of these incisional procedures. Drawbacks of traditional incisional procedures include unpredictable IOP-lowering results, prolonged visual recovery, long-term risk of infection and vision loss, frequency of follow-up visits, and long-term failure rate. Such procedures may also involve additional equipment cost and, in some cases, a steep learning curve. The added equipment cost in particular presents a significant hurdle to providers, hospitals, and surgery centers that may require several procedures to recoup the initial investment. Providers and patients may also face opposition from insurance companies regarding coverage of a procedure lacking long-term efficacy data. The requirement for additional equipment also limits patient access to these procedures in underserved areas of the world.

A goniotomy is generally referred to as a surgical procedure used to treat glaucoma. Glaucoma can be caused by blockage in the trabecular meshwork and/or a developmental arrest of some of the structures within the anterior (front) segment of the eye. These changes lead to an excess of fluid in the eye, which can cause pressure that can damage the internal structures of the eye leading to optic neuropathy and loss of vision.

One type of glaucoma that can be treated with goniotomy is known as congenital glaucoma. Congenital glaucoma is caused by a decrease in or even a complete obstruction of the outflow of intraocular fluid. The ocular syndromes and anomalies that predispose a child to congenital glaucoma include the following: Reiger's anomaly; Peter's anomaly; Axenfeld's syndrome; and Axenfeld-Rieger's syndrome. Systemic disorders that affect the eyes in ways that may lead to glaucoma include Marian's syndrome; rubella (German measles); and the phacomatoses, which include neurofibromatosis and Sturge-Weber syndrome. Since these disorders affect the entire body as well as the eyes, the child's pediatrician or family doctor will help to diagnose and treat these diseases.

One purpose of a goniotomy is to clear the obstruction to aqueous outflow from the eye, which in turn lowers the intraocular pressure ("TOP"). This is a treatment method for any type of glaucoma including primary open angle glaucoma and chronic angle closure glaucoma.

Before the surgeon begins the procedure, the patient may be given miotics, which are drugs that cause the pupil to contract. The partial closure may improve the surgeon's view of and access to the trabecular meshwork; it may also protect the lens of the eye from trauma during surgery. Other drugs may be administered to lower the intraocular pressure. Goniotomy procedures may be done without use of miotics. In some embodiments, devices may be used in the setting of a dilated (non-miotic) pupil, as can devices described as prior art.

Once the necessary drugs have been given and the patient is anesthetized, the surgeon may use forceps or sutures to stabilize the eye in the correct position. The patient's head may be rotated away from the surgeon so that the interior structures of the eye are more easily seen. Next, with either a knife-needle or a goniotomy knife, the surgeon punctures the cornea while looking at the interior of the eye through a microscope or a loupe. An assistant may use a syringe to introduce fluid into the eye's anterior chamber through a viscoelastic tube as the surgeon performs the goniotomy.

A gonioscopy lens may be then placed on the eye. As the eye is rotated by an assistant, the surgeon sweeps the knife blade or needle through 90-120 degrees of arc in the eye, making incisions in the anterior trabecular meshwork, avoiding the posterior part of the trabecular meshwork in order to decrease the risk of damage to the iris and lens. Endoscopic visualization may also be used to guide cutting. In some embodiments, devices may be placed at the end of an endoscope, precluding the need for a gonio lens during treatment.

Once the knife and tubing are removed, saline solution may be introduced through the hole to maintain the integrity of the eye and the hole is closed with sutures. The surgeon then applies antibiotics and corticosteroids to the eye to prevent infection and reduce inflammation. The head may be then rotated away from the incision site so that blood cannot accumulate. The second eye may be operated on at the same time. If the procedure needs to be repeated, another area of the eye may be treated.

It is desirable to provide simple, inexpensive, and accurate instruments useable to perform the procedure of cutting the TM in the eye and effectively remove a complete full thickness strip of TM without leaving TM leaflets as well as other procedures where it is desired to remove a strip of tissue from a larger mass of tissue.

A goniotomy is simply an incision of the TM to cut it into two leaflets, it is the basic form of cutting TM that all other devices are trying to improve upon. Since it is just an incision, it leaves the entire tissue behind (albeit segmented) and then the tissue scars down and the eye pressure goes up anyway. This may be why "newer" devices are trying to cut and remove the actual TM from the area over Schlemm's canal. The complete removal of TM without leaving leaflets is one key feature differentiating embodiments of the present disclosure from conventional blade goniotomy (e.g., using an MVR blade). The anatomical design of the device of the present disclosure may be better suited for effective removal of complete strips of tissue, in particular the TM, with minimal to no traumatic impact on the surrounding tissue.

Specific advantages of some embodiments described herein as compared to other, conventional devices include but are not limited to:
1. No mechanically moving parts
2. No cautery or burning of tissue
3. Two blades are in place on the sides of the device that cut the trabecular meshwork (TM) in a precise fashion leaving little TM behind (current devices leave a lot of TM behind that then scars over)
4. The entry into Schlemm's canal is done with use of the blade tip similar to what has been described for decades in standard goniotomy. Other devices use a non-blade footplate to enter Schlemm's canal.
5. The dimensions of the device allow for complete cutting and fit in Schlemm's canal with precision.
6. The tip of the blade ramps up to the two side blades to present the TM to the two side blades, which then allows for more precise cutting.
7. The sides of the ramp are devoid of blades or cutting features until the point where the dual blades are present.
8. Cutting of the TM with the dual blades occurs at points elevated from the natural resting position of the TM.

Referring now to FIG. 1, a device 12 can include dual cutting blades (black arrows) as well as the distal point (asterisk) that is designed to pierce the trabecular meshwork ("TM") and enter into the Schlemm's canal. Once in the canal, the device is advanced so that the TM moves up the ramp from the distal point toward the dual cutting blades, which then cleanly incise the presented TM. The distance between the dual blades is designed to closely match that of the width of the TM across a range of human eyes.

Referring now to FIGS. 2-5, the device 12 can include a handle 1, a first interface 2, a tool shaft 3, a second interface 4, and a platform 5. The platform can include and/or form an insertion tip 6, a posterior end 7, a first side 8, a second side 9, a first blade 10, and a second blade 11.

In some embodiments, the device 12 comprises: a handle 1 that necks down to a tool shaft 3 by a first interface 2 wherein the tool shaft widens into a platform 5 by a second interface 4. The platform 5 comprises an insertion tip 6 on a distal end of the platform 5. The platform 5 can be beveled and include a ramp 13 (FIG. 7) from the insertion tip 6 back towards the posterior end 7 the platform 5, and a first lateral element (e.g., blade) 10 and second lateral element (e.g., blade) 11 along the sides of the platform 5. In some embodiments, the sides of the platform 5 comprise a first side 8 and a second side 9. In some embodiments, the platform 5 includes a first side 8 extending from the proximal side of the platform 5 to the distal side of the platform 5 and a second side 9 extending from the proximal side of the platform 5 to the distal side of the platform 5. In some embodiments, the first side 8 and the second side 9 each form a bevel of the platform 5. In some embodiments, the first side 8 and the second side 9 each form a convex portion of the platform 5. In some embodiments, proximal segments of the first side 8 and the second side 9 are parallel to each other and distal segments of the first side 8 and the second side 9 intersect at the tip 6. In some embodiments, the first lateral element extends from the first side and the second lateral element extends from the second side.

In some embodiments, the first lateral blade 10 and second lateral blade 11 are in a perpendicular alignment to the bottom of the platform. In some embodiments, the first and second lateral blades 10 and 11 are straight. In some embodiments, the first and second lateral blades 10 and 11 are parallel to each other.

In some embodiments, the ramp 13 increases from a distal width at the distal side (e.g., at the tip 6) to a proximal width, greater than the distal width, at the proximal side (e.g., adjacent to the lateral blades 10 and 11). The ramp 13 can be planar, concave, and/or convex. Where the ramp 13 is planar, it can provide a gradual stretching of TM that is elevated by the platform 5 and across the ramp 13. In some embodiments, a maximum width across the first and second lateral elements is not less than a maximum width across the ramp. This allows the incisions to be made at the outer peripheries of the platform, where the first side 8 and the second side 9 elevate and present the TM to the lateral blades 10 and 11.

In some embodiments, the device 12 includes a bottom surface 15 that is configured to abut the outer wall of the Schlemm's canal 22 during a procedure. The bottom surface 15 can be planar, convex, concave, or combinations thereof. For example, the bottom surface 15 can include a concave portion between at least two lateral edges. For example, lateral edges can be provided below the first side 8 and the second side 9 of the ramp 13, with a concave portion formed between the lateral edges. The lateral edges can make contact with the outer wall of the Schlemm's canal 22 during a procedure.

Figure 3:
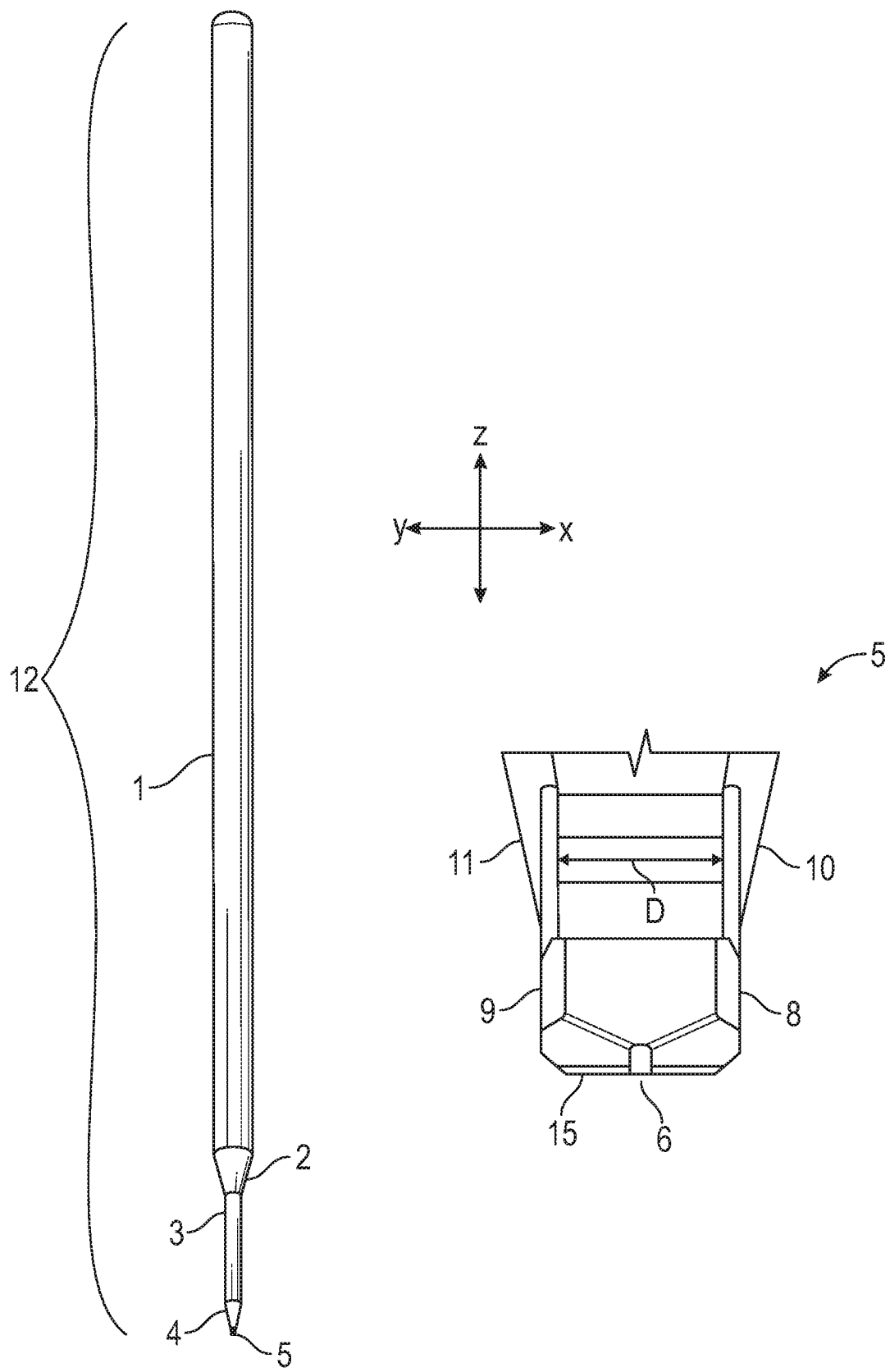
FIG. 3 shows front view of a device with an enlarged detailed view of the operative end of the device.
Figure 4:
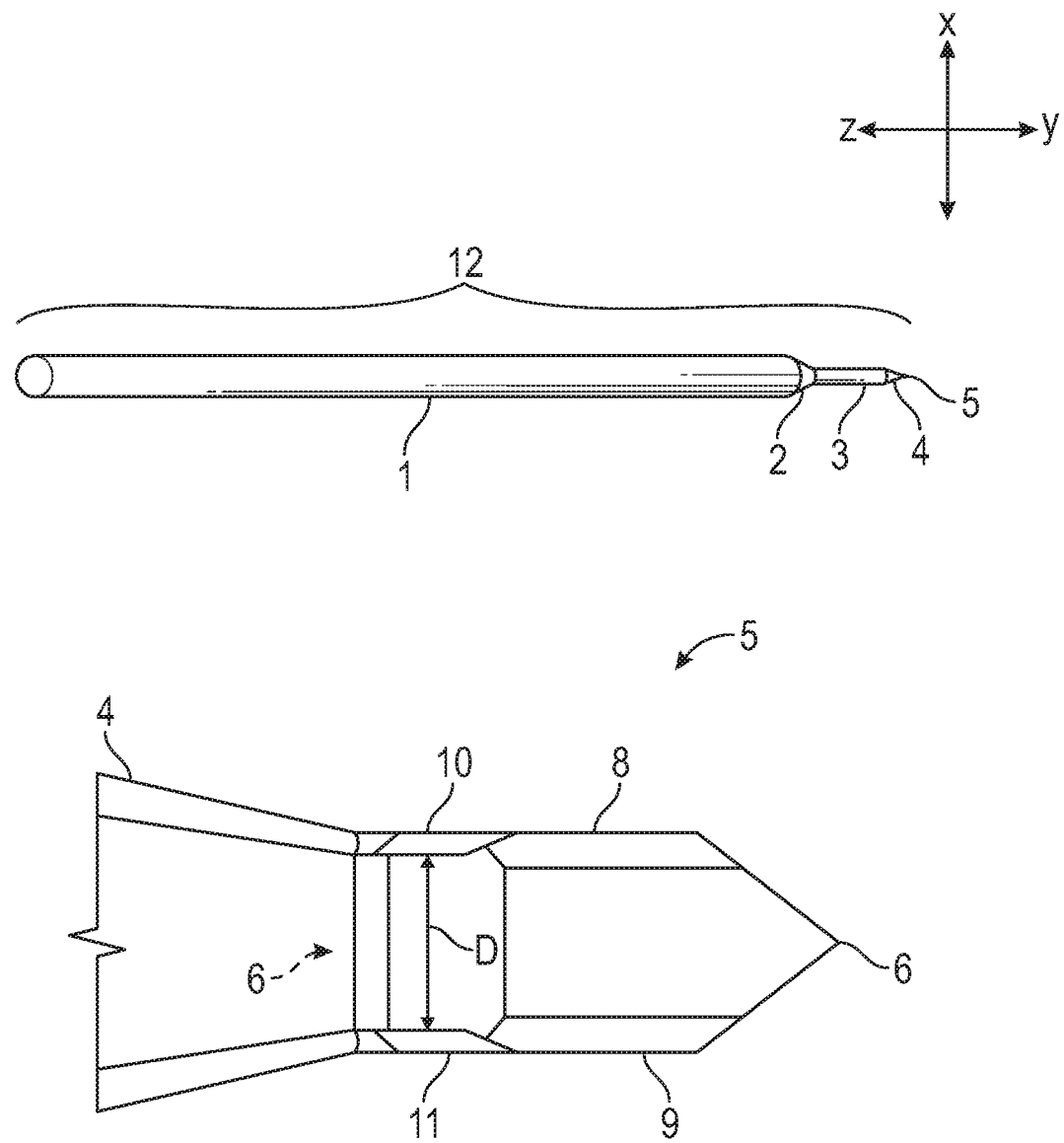
FIG. 4 shows a top view of a device with an enlarged detailed view of the operative end of the device.

As shown in FIG. 3, the platform 5 can increase in thickness from the second side 9 towards the first side 8 in the direction of the X-axis. In some embodiments, the platform 5 increases in thickness from the second side 9 towards the first side 8 in the direction of the X-axis and the platform 5 increases in thickness from a fine blade tip of the first end 6 towards the posterior end 7 of the platform 5 in the direction of the Y-axis.

Figure 5:
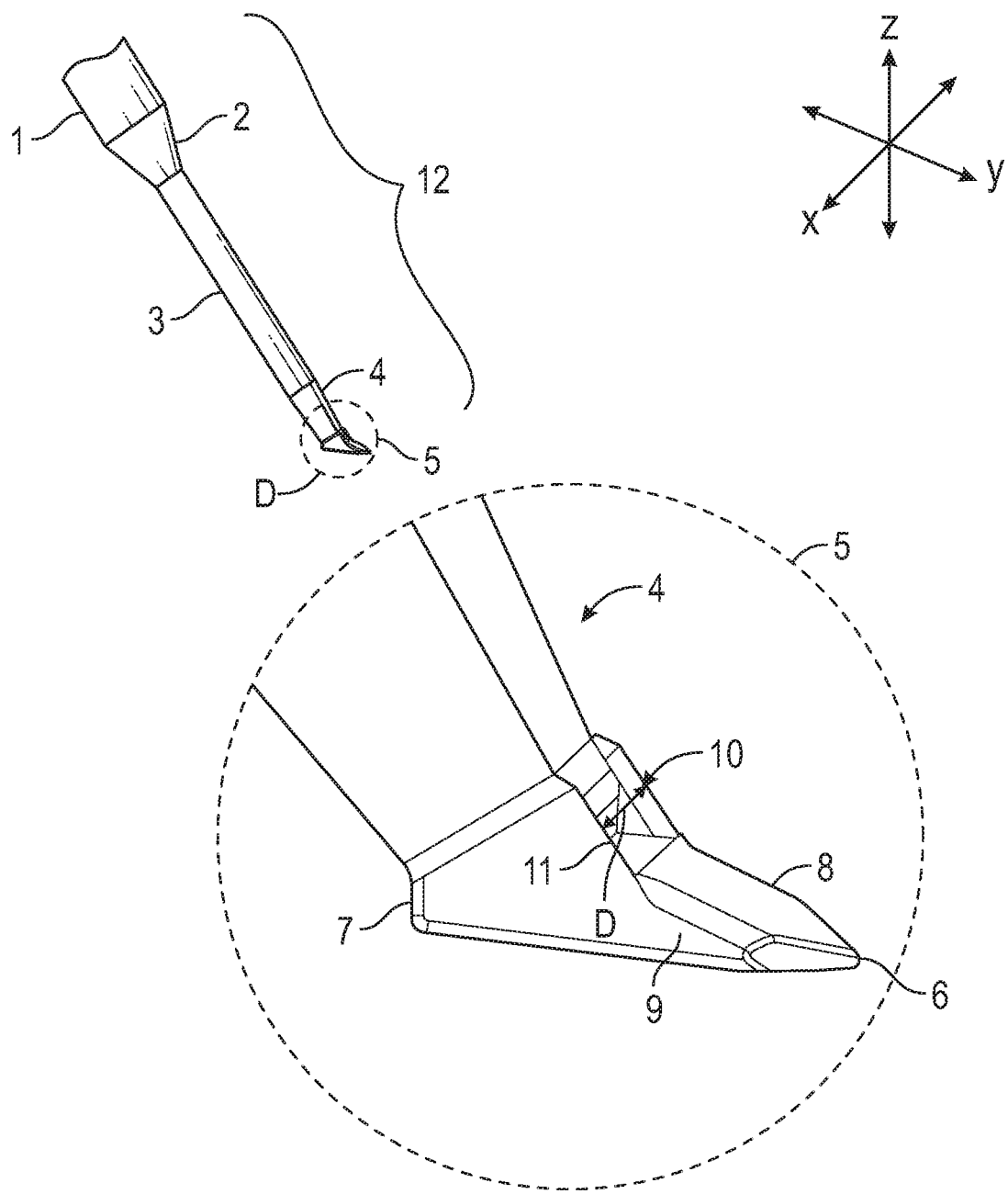
FIG. 5 shows perspective view of a device with an enlarged detailed view of the operative end of the device. The shaded aspect provided a view of the dimensions of the platform.

Referring now to FIG. 5, in some embodiments, the platform 5 is set at a specific angle and orientation relative to the handle 1. In some embodiments, a device 12 comprises a handle 1 and a platform 5, wherein the platform 5 freely rotates in at least two dimensions. In some embodiments, the handle 1 and platform 5 are operably attached at an angle ranging between 90 and 120 degrees in the Y-Z axis. In some embodiments, the handle 1 and platform 5 are operably attached at an angle ranging between 90 and 180 degrees in the X-Z axis. In some embodiments, the platform 5 freely rotates in an X-Y dimension relative to the handle 1. In some embodiments, the platform 5 remains at a fixed angle in the X-Y, X-Z, and Y-Z dimensions relative to the handle 1. In some embodiments, the platform 5 freely rotates in a positive Z dimension relative to the handle 1.

In some embodiments, the platform 5 comprises an insertion tip 6 and a posterior end 7 of the platform 5, wherein the posterior end 7 of the platform 5 is between 2 and 30 times greater in thickness relative to the insertion tip 6. The thickness can be measured along the Z-axis, such as through a surface of the ramp 13 and the base of the platform 5. In some embodiments, the dimensions of the platform 5 are dictated by the formula $A^2+B^2=C^2$, wherein A is the length of the platform 5 from the insertion tip 6 to the back of the platform 7, B is the height of the platform 5 and C is the length of the ramp formed by the platform insertion tip up to the height of the platform. In some embodiments, the height of the platform 5 is not to exceed 0.5 millimeters. In some embodiments, the length of the platform 5 from the insertion tip 6 to the back of the platform 7 is not to exceed 1.0 millimeters. In some embodiments, the width of the platform 5 is not to exceed 0.35 millimeters. In some embodiments, the insertion tip 6 comprises a fine surgical lancet. In some embodiments, the insertion tip 6 comprises an angle of between 20 and 90 degrees. In some embodiments, the platform 5 increases in thickness from a fine blade tip towards the posterior end 7 of the platform 5 in the direction of the Y-axis.

In some embodiments, the insertion tip 6 comprises a pointed tip with fine edges of surgical sharpness. In some embodiments, the insertion tip 6 comprises a lancet. In some embodiments, the platform 5 further comprises a first blade 10 and a second blade 11. In some embodiments, the first blade 10 is attached to a first side 8 of the posterior end 7 of the platform 5. In some embodiments, the first blade 10 and platform 5 are operably attached at an angle ranging between 90 and 180 degrees in the Y-Z axis. In some embodiments, the angle is preferably between 90 and 120 degrees in the Y-Z axis. In some embodiments, the second blade 11 and platform 5 are operably attached at an angle ranging between 90 and 120 degrees in the Y-Z axis. In some embodiments, the first blade 10 and handle 1 are operably positioned at an angle ranging between 90 and 120 degrees in the Y-Z axis. In some embodiments, the second blade 11 and handle 1 are operably positioned at an angle ranging between 90 and 120 degrees in the Y-Z axis. In some embodiments, the second blade 11 is attached to a second side 9 of the posterior end 7 of the platform 5. In some embodiments, the first blade 10 and the second blade 11 are positioned at an angle between approximately 100 to 140 degrees relative to the top surface of the posterior end 7 of the platform 5.

In some embodiments, the first blade 10 and the second blade 11 are parallel. In some embodiments, the first blade 10 and the second blade 11 extend above the top surface of the posterior end 7 of the platform 5. In some embodiments, the platform 5 is approximately 0.3 millimeters wide. In some embodiments, the platform 5 is approximately 0.2 millimeters wide. In a preferred embodiment, the platform 5 is approximately 0.25 millimeters wide. In some embodiments, the platform 5 is approximately 1.0 millimeters long. In some embodiments, the platform 5 is approximately 0.4 millimeters high. In some embodiments, the highest point on the platform 5 is the first and second blades. The device 12 may be provided as a pre-sterilized, single-use disposable probe or tip that is attachable to a standard surgical handpiece.

It is not intended that embodiments of the present disclosure be limited to any particular construction material; however, it is believed that preferred materials include titanium, stainless steel, polyether ether ketone (PEEK), shape memory alloy, and shape memory polymers. In some embodiments, the present device is made from metal alloy materials. In some embodiments, the device of the present disclosure is rigid at room temperature, but is more flexible at body temperature. In some embodiments, the portions of the device of the present disclosure are rigid at room temperature, but are more flexible at body temperature. In some embodiments, portions of the device are made from different materials. In some embodiments, portions of the device are made from materials of various rigidity. In some embodiments, the tool shaft is flexible. In some embodiments, the tool shaft is made from a lower density material.

The tip may be formed of various metals or polymers that are rigid enough to support elevation of tissue such as TM. The blades may be made of the same materials as the distal tip and handle 1 or might be of a separate material that allows for greater tolerances for a razor edge (stainless steel or titanium). Shape memory polymers or alloys could be utilized to enhance functionality of the device by allowing for a change in confirmation after placing the device in the eye and exposing it to body heat. A movable sheath might be employed to cover the distal cutting tip during the insertion and removal steps from the eye so that the tip is not injured by movement across the clear corneal wound. The device can be made of different colors such as blue or black so that it can be visualized through the semi translucent TM tissue for better guidance.

Figure 6:
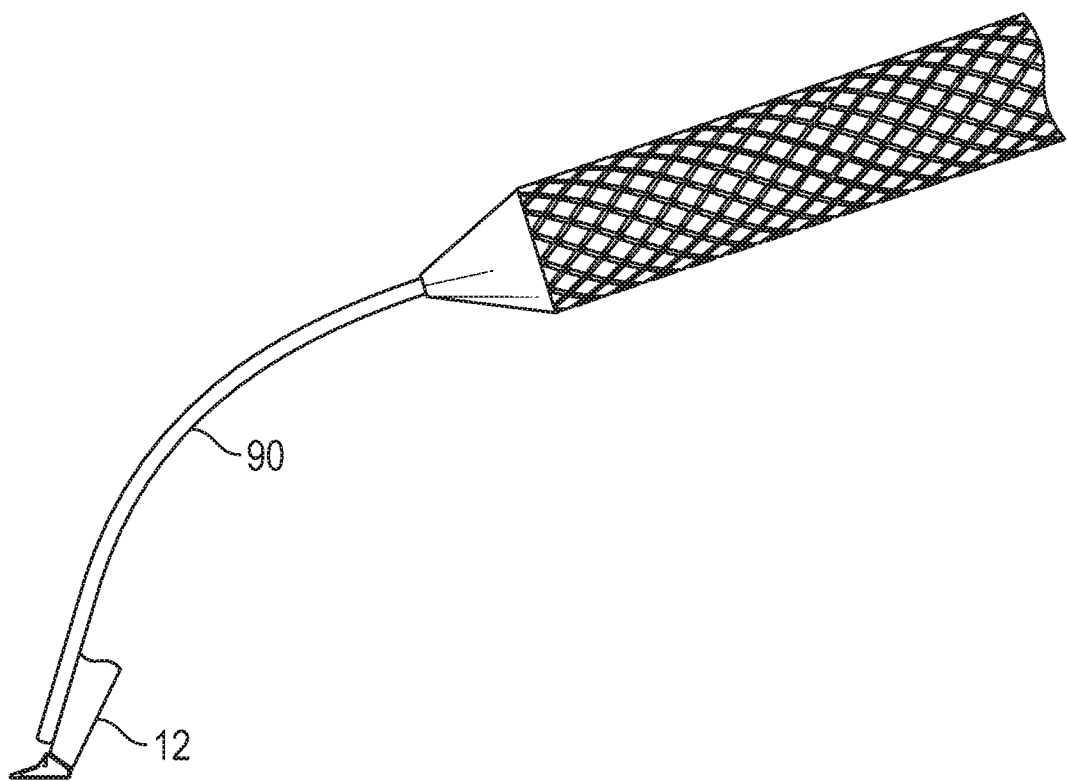
FIG. 6 shows a plan view of a device integrated onto an endoscope.

Referring now to FIG. 6, endoscopic visualization may also be used to guide the cutting. In some embodiments, the device 12 of the present disclosure may be placed at the end of an endoscope 90, precluding the need for a gonio lens during treatment. In some embodiments, the device of the present disclosure may be placed at the end of an endoscope 90 and the TM may be engaged under direct visualization of the endoscope camera. It is not intended that embodiments of the present disclosure be limited to any particular endoscope; it is believed that the device may be optimally designed for an ophthalmic endoscopy system endoscope.

The device could have a distal port that allows for injection of fluid to deliver local balanced salt solution, medication, viscoelastics, and/or therapeutic agents or to wash away reflux of blood that occurs during this type of procedure. For example, the device 12 and/or the endoscope 90 can be used to inject fluid (e.g., solution, medication, viscoelastics, and/or therapeutic agents). The ultimate goal of this procedure may be to remove entire segments of TM without leaving significant leaflets of tissue behind (something that occurs with other devices that cut TM without conforming to the space of interest). The procedure might be combined with cataract extraction and can be performed before or after the cataract extraction and while the pupil is dilated. The procedure might be coupled with other intraocular surgery such as iris or vitreous/retina based procedures.

Referring now to FIGS. 7-10, devices disclosed herein can be used for incising tissue, such as a trabecular meshwork. A device may be introduced through a clear corneal incision (incision size between 0.5 and 2.8 mm in width) and advanced through the anterior chamber either across the pupil or across the body of the iris to engage the trabecular meshwork (TM) on the opposite side of the anterior chamber. The anterior chamber may be filled with viscoelastic to stabilize the chamber during the procedure. As shown for example in FIG. 7, once the target tissue 20 (e.g., TM) is reached, the tip 6 of the device may be then used to enter into Schlemm's canal ("SC") 22.

Figure 7:
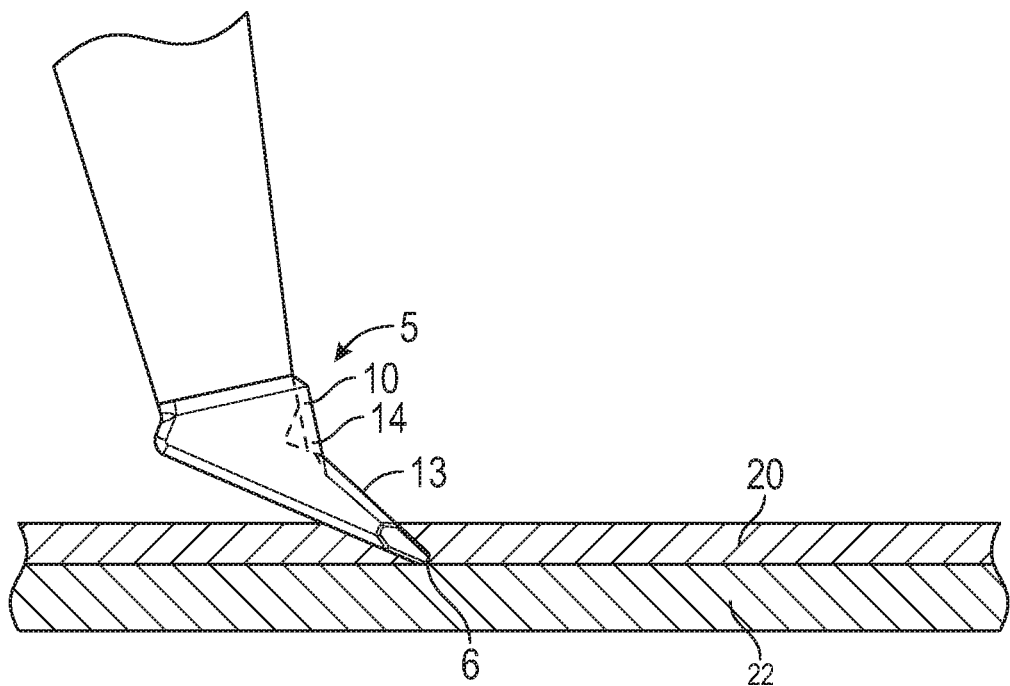
FIG. 7 shows a side view of a device applied to a trabecular meshwork and Schlemm's canal, according to some embodiments of the present disclosure.
Figure 8:
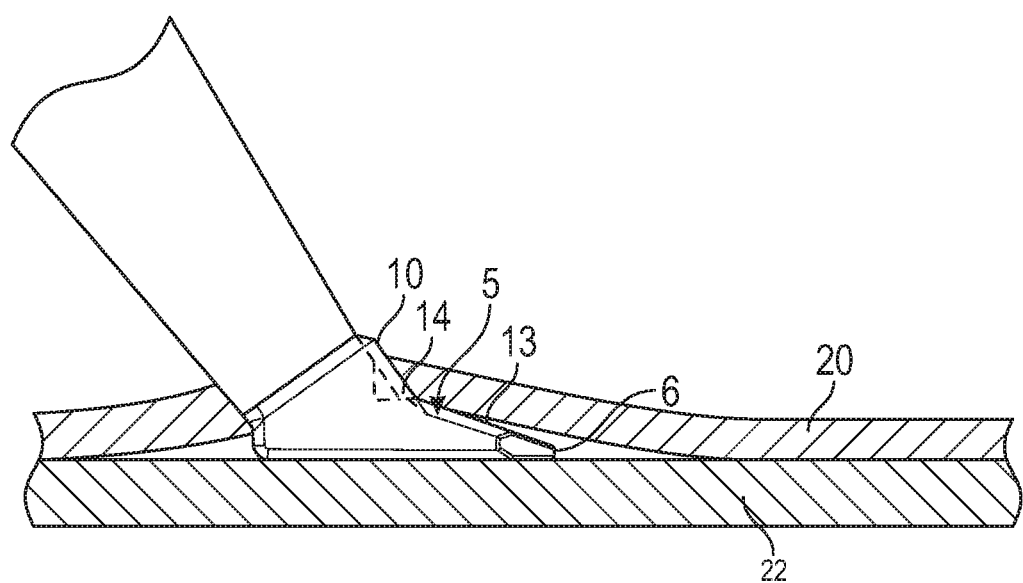
FIG. 8 shows a side view of a device elevating the trabecular meshwork away from the Schlemm's canal, according to some embodiments of the present disclosure.
Figure 9:
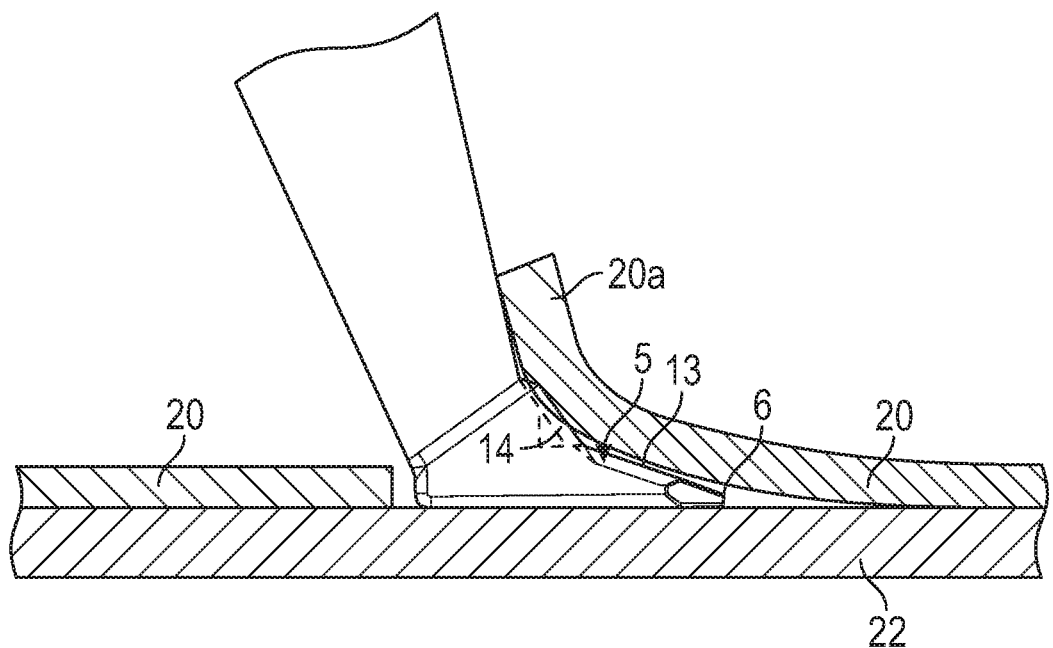
FIG. 9 shows a side view of a device incising the trabecular meshwork, according to some embodiments of the present disclosure.
Figure 10:
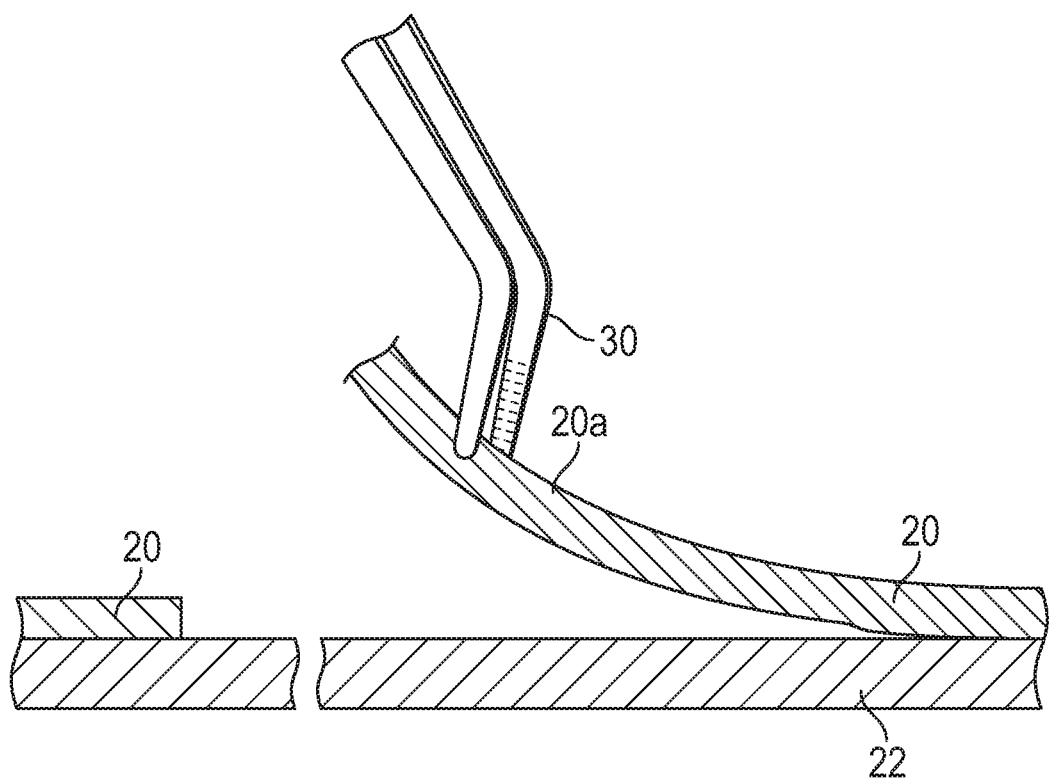
FIG. 10 shows a side view of a device engaging a strip of trabecular meshwork, according to some embodiments of the present disclosure.

According to some embodiments, for example as shown in FIG. 7, the ramp 13 may be used to elevate the TM 20 away from the outer wall of the Schlemm's canal 22. According to some embodiments, for example as shown in FIG. 8, the advancement of the platform 5 can stretch the TM 20 as it travels up the ramp 13 without tearing a strip 20a of the TM 20 that is on the ramp 13. For example, the first side 8 and the second side 9 can allow the TM 20 on the ramp 13 (e.g., distal to the first and second lateral blades 10 and 11) to remain connected to the TM 20 that is not elevated by the ramp 13. As the TM 20 is elevated, it is under tension that is greater than the tension of the TM 20 when not elevated from the SC 22. Advancement of the ramp 13 facilitates presentation of the TM 20 to the first and second lateral blades 10 and 11. According to some embodiments, for example as shown in FIG. 9, the TM 20 contacts the first and second lateral blades 10 and 11 while the TM 20 is elevated (e.g., stretched and/or under tension). In this configuration, the first and second lateral blades 10 and 11 incise first and second incisions into the TM 20 to form the strip 20a of the TM 20. The incision is more easily and precisely made due to the elevation of the TM 20. During advancement of the platform 5, at least a portion of the strip 20a can be received within the gap 14 between the first and second lateral blades 10 and 11. The strip 20a can have a width W that corresponds to the distance D across the gap 14. The width W can be measured along the X-axis, such as across the first and second incisions and transversely (e.g., orthogonally) to the direction of advancement of the device 12 to form the strip 20a. The distance D can be measured along the X-axis, such as across the first and second lateral blades 10 and 11 and transversely (e.g., orthogonally) to the direction of advancement of the device 12 to form the strip 20a. According to some embodiments, for example as shown in FIG. 10, the strip 20a that has been separated from a remainder of the TM 20 can be removed by a device 30 (e.g., forceps) or by aspiration.

The advancement of the platform 5 and the ramp 13 can proceed as the device advances clockwise or counterclockwise. The distal cutting portion is angled so that the dual blades are placed in optimum cutting position. This angle may be such that the cutting tip bends to conform to the area between Schwalbe's line and the scleral spur (SS), an area that encompasses SC. SC is narrow near the cornea and wider near the SS and thus an angled tip is best to present the tissue 20 to the two edges of the TM. The ramp 13 of the cutting tip may be angled so that the tissue 20 is constantly elevated towards the blade as the tip is advanced in circumferential pattern. Between the cutting tip and the first and second lateral blades 10 and 11, the ramp 13 is shaped to avoid cutting tissue, such that the TM 20 that is elevated away from the outer wall of the Schlemm's canal 22 remains intact as it advances along the ramp 13. For example, the ramp 13 can include convex or beveled edges that are not sharp enough to cut the TM 20.

In some embodiments, a method for cutting a strip 20a of tissue 20 (e.g., TM) of width W from a tissue mass comprises the steps of: a) providing a device which comprises; i) a handle attached to a platform, ii) an anterior insertion tip of the platform expanding backwards to a posterior end of the platform that is devoid of cutting features, iii) a first side of the platform upon which is affixed a first lateral blade, iv) a second side of the platform upon which is affixed a second lateral blade; v) at least first and second lateral cutting edges formed by blades in a generally perpendicular and posterior position to the opposite edges of the anterior insertion tip of the platform, the first and second cutting edges being separated by a gap 14 of distance D that is approximately equal to the width W of the strip 20a of tissue 20 to be cut; b) advancing the anterior insertion tip of the platform through tissue 20 such that the first and second cutting edges are positioned adjacent to tissue 20 to be cut; c) advancing the distal end such that the cutting edges cut a strip 20a of tissue 20 of approximate width W and the cut strip 20a of tissue 20 remains substantially intact. In some embodiments, the mass of tissue 20 is in vivo. In some embodiments, the mass of tissue 20 is in vitro. In some embodiments, the device is integrated into an endoscope. In some embodiments, the cutting is under direct visualization. In some embodiments, the mass of tissue 20 is located within the body of a human or animal subject. In some embodiments, the strip 20a of tissue 20 is removed for a diagnostic or therapeutic purpose. In some embodiments, the subject suffers from glaucoma and wherein the method is carried out to remove a strip 20a of trabecular meshwork from an eye of the subject to facilitate drainage of aqueous humor from the eye thereby lowering intraocular pressure. In some embodiments, the eye has a dilated pupil. In some embodiments, step b comprises inserting the device into the anterior chamber of the eye; positioning the anterior insertion tip of the platform adjacent to or within the trabecular meshwork of the eye; and advancing the cutting tube such that the cutting edges cut a strip 20a of approximate width W from the trabecular meshwork. In some embodiments, the device provided in step a of the method further comprises an anterior insertion tip of the platform and wherein the anterior insertion tip of the platform is advanced through the trabecular meshwork and into Schlemm's canal and, thereafter, the anterior insertion tip of the platform is advanced through Schlemm's canal as the cutting tube is advanced to cut the strip 20a of tissue 20. In some embodiments, the device provided in step a) further comprises apparatus for severing the strip 20a of tissue 20 after the strip 20a of tissue 20 has reached a desired length and wherein the method further comprises the step of severing the strip 20a of tissue after the strip 20a of tissue 20 has reached a desired length. In some embodiments, the method is carried out to form an incision in skin, mucous membrane, an organ, a tumor or other anatomical structure. In some embodiments, the method is carried out to remove tissue 20 from the vascular system. In some embodiments, the method is carried out to remove tissue 20 from the lymphatic system. In some embodiments, the method further comprises the step of: c) removing the strip 20a of tissue 20.

Figure 11:
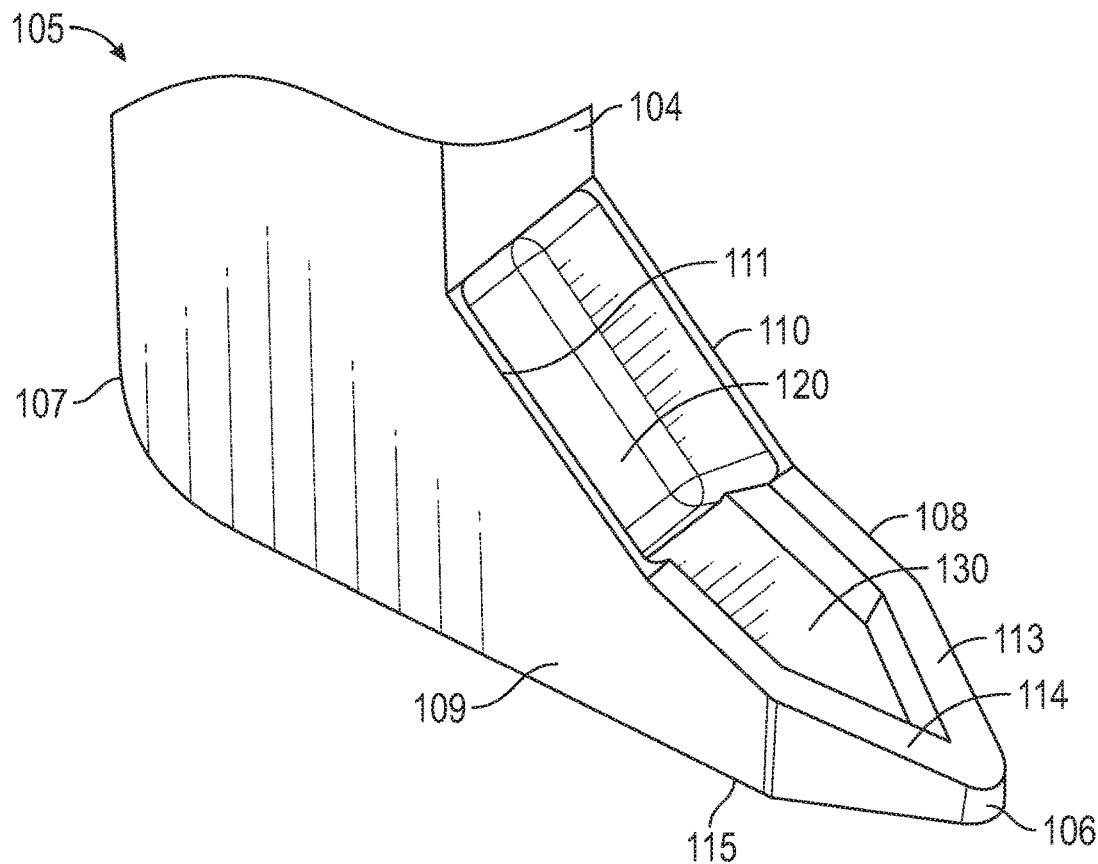
FIG. 11 shows a perspective view of an example of a device according to embodiments of the present disclosure.
Figure 12:
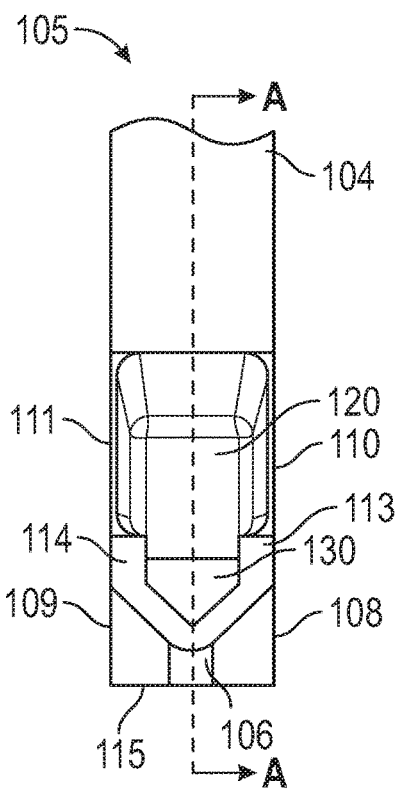
FIG. 12 shows a front view of the device of FIG. 11.
Figure 13:
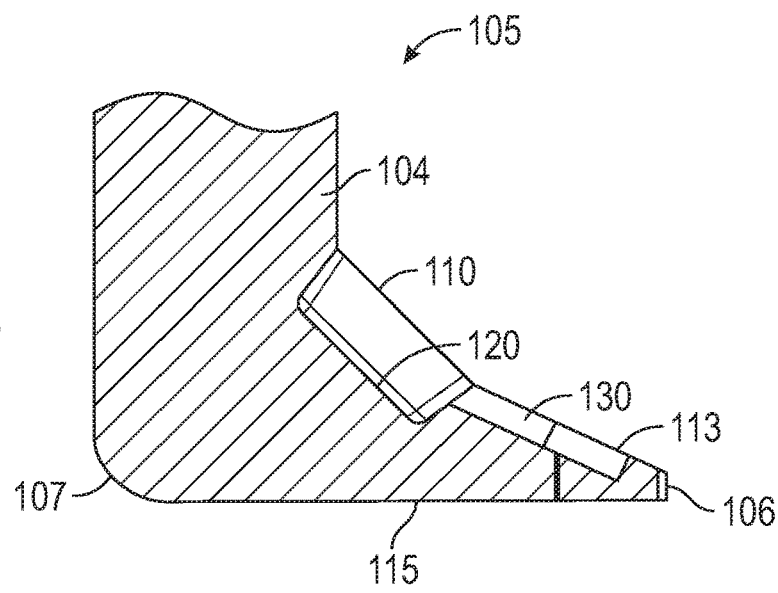
FIG. 13 shows a sectional side view of the device of FIG. 11.

Referring now to FIGS. 11-13, a device having a platform 105 can include some features similar to those of the device 12 illustrated in other figures. As shown in FIG. 11, a platform 105 of the device can extend from a shaft 104 and include a tip 106 at a distal side of the platform 105 and first and second walls 113 and 114 extending from the distal side of the platform 105 to a proximal side of the platform 105, opposite the distal side of the platform 105. For example, the first and second walls 113 and 114 can extend from the tip 106 to lateral elements 110 and 111, respectively.

As further shown in FIG. 11, the first and second walls 113 and 114 can at least partially surround a recessed portion 130. The recessed portion 130 can be positioned at an elevation that is lower (e.g., closer to the bottom surface 115) than are the first and second walls 113 and 114. The first and second walls 113 and 114 can extend above (e.g., farther from the bottom surface 115) the recessed portion 130. Accordingly, a space can be defined above the recessed portion 130 and at least partially surrounded by the first and second walls 113 and 114. For example, the platform 105 can have a height at the tip 106, defined by a distance between the top surfaces of the first and second walls 113 and 114 and the bottom surface 115. By further example, the platform 105 can have a height at the recessed portion 130, defined by a distance between the recessed portion 130 and the bottom surface 115. The height of the platform 105 at least a portion of the recessed portion 130 can be smaller than the height of the platform 105 outside the recessed portion 130 (e.g., defined in part by the by the first and second walls 113 and 114). While both heights can vary along the length of the platform 105, it will be understood that, at any given location along the length (e.g., Y-axis), the height of the first and second walls 113 and 114 can be larger than the height at the recessed portion 130. Additionally, a height at the distal most end of the recessed portion 130 can be smaller than a height of at least a portion of the first and second walls 113 and 114 that is distal to the recessed portion 130. Accordingly, trabecular meshwork received over the first and second walls 113 and 114 and onto the recessed portion 130 is permitted to drop downward into the space below the height of the first and second walls 113 and 114 and above the height of the recessed portion 130.

Even with the presence of the recessed portion 130 and the gap 120 between the lateral elements 110 and 111, the platform 105 can provide continuous structure defining a height at every point along the length thereof between the tip 106 and the posterior end 107. Likewise, the platform 105 can provide continuous structure defining a height at every point along the width thereof between the opposing sides 108 and 109.

The recessed portion 130 can define a surface that faces in a direction that is generally away from the bottom surface 115, including directions that are not perpendicular to the bottom surface 115. For example, the surface of the recessed portion 130 can be parallel to the top surfaces of the first and second walls 113 and 114, so that each forms a sloped ramp with increasing height along the length of the platform 105 extending away from the tip 106. Additionally or alternatively, the recessed portion 130 can define other surface shapes and/or features. For example, a surface of the recessed portion 130 can be planar, multi-planar (e.g., in the X- and Y-axes), convex, concave, or combinations thereof.

The first and second walls 113 and 114 and the recessed portion 130 can be joined together by one or more transition sections. Such transitions can be stepwise with a surface that is generally perpendicular to the recessed portion 130. While a stepwise transition is shown in FIGS. 11-13, such transitions can include one or more other shapes, including bevel, curved, round, chamfer, fillet, and/or combinations thereof.

The recessed portion 130 can extend across a proximal region of the platform 105 and/or a distal region of the platform 105. For example, the recessed portion 130 can extend from the gap 120 toward the tip 106 at the distal end of the platform 105. By further example, the recessed portion 130 can extend from a position near the tip 106 toward the posterior end 107 of the platform 105. The depth of the gap 120 between the lateral elements 110 and 111 (i.e., as defined by the later elements) can be greater than a depth of the space above the recessed portion 130 (i.e., as defined by transition sections about the recessed portion 130).

The transition sections defining the periphery of the space above the recessed portion 130 can be substantially parallel to nearby portions of the opposing sides 108 and 109. For example, the transition sections can be substantially parallel to each other along a proximal region of the recessed portion 130, near the gap 120 between the lateral elements 110 and 111. By further example, the transition sections can converge towards each other along a distal region of the recessed portion 130, near the tip 106.

As shown in FIGS. 11 and 12, opposing sides 108 and 109 of the platform 105 can extend downwardly from the first and second walls 113 and 114, respectively. The opposing sides 108 and 109 can be planar and/or parallel to each other. The first and second walls 113 and 114 can transition to the opposing sides 108 and 109 with a transition feature. While a sharp transition is shown in FIGS. 11 and 12, the transition feature can have one or more other shapes, including bevel, curved, round, chamfer, fillet, etc. Along the transition features, the width of the platform 105 can optionally transition from a first width, between the opposing sides 108 and 109, to a second width, less than the first width, across the tops of the first and second walls 113 and 114. The transition from the first width to the second width can be gradual, linear, stepwise, or another type of transition.

A transition feature can be provided between the bottom surface 115 and the opposing sides 108 and 109. For example, the bottom surface 115 can transition to the opposing sides 108 and 109 with transition sections. While a sharp transition is shown in FIGS. 11 and 12, the transition feature can have one or more other shapes, including bevel, curved, round, chamfer, fillet, etc. Along the transition features, the width of the platform 105 can optionally transition from a first width, between the opposing sides 108 and 109, to a second width, less than the first width, across the bottom surface 115. The transition from the first width to the second width can be gradual, linear, stepwise, or another type of transition.

The platform 105 can include the bottom surface 115 extending from the tip 106 at the distal side of the platform 105 to a posterior end 107 of the platform 105, opposite the tip 106. The bottom surface 115 of the platform 105 can be positioned opposite the top surfaces of the first and second walls 113 and 114. The bottom surface 115 can be configured to abut the outer wall of the Schlemm's canal during a procedure (see FIGS. 7-10). At least a portion of the bottom surface 115 can be flat and/or planar. Additionally or alternatively, the bottom surface 115 can be planar, convex, concave, or combinations thereof. For example, the bottom surface 115 can include a recessed portion (not shown) between at least two protrusions. The recessed portion can be defined by a gap, space, or void. Additionally or alternatively, adjacent to the tip 106, the bottom surface 115 can provide a continuous (e.g., planar) portion that is not interrupted by any recessed portion. Accordingly, the bottom surface 115 can optionally include both a planar (e.g., distal) portion and a non-planar (e.g., proximal) portion along the length thereof. The posterior end 107 can define a curved or round surface that transitions from the bottom surface 115 to a portion of the shaft 104.

The first and second walls 113 and 114 can support elevation of trabecular meshwork without cutting thereon. For example, the first and second walls 113 and 114 can include segments that each have a width greater than a width of the lateral elements 110 and 111. As the trabecular meshwork is stretched over the first and second walls 113 and 114, it can remain intact while brought to the lateral elements 110 and 111. Additionally, as the trabecular meshwork is stretched over the first and second walls 113 and 114, it will be further stretched over the recessed portion 130, which will provide a space between segments of the first and second walls 113 and 114. The space above the recessed portion 130 can guide portions of the trabecular meshwork toward the gap 120 between the lateral elements 110 and 111.

Figure 14:
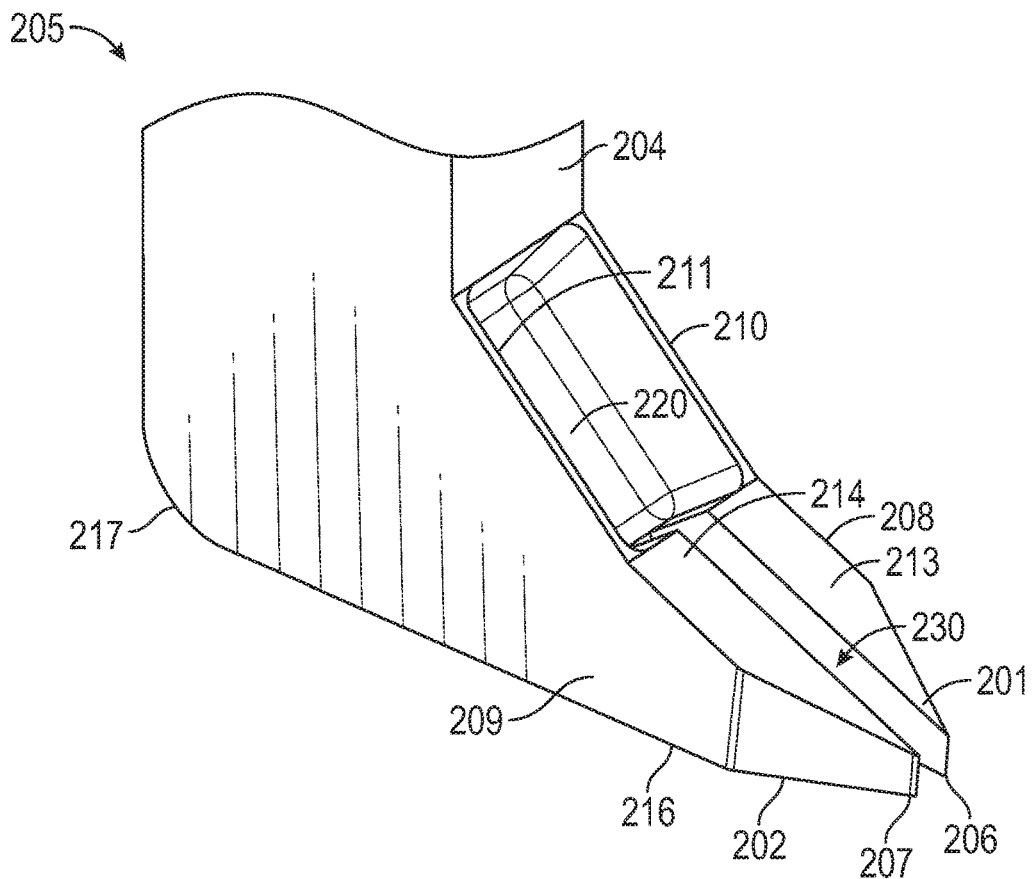
FIG. 14 shows a perspective view of an example of a device according to embodiments of the present disclosure.
Figure 15:
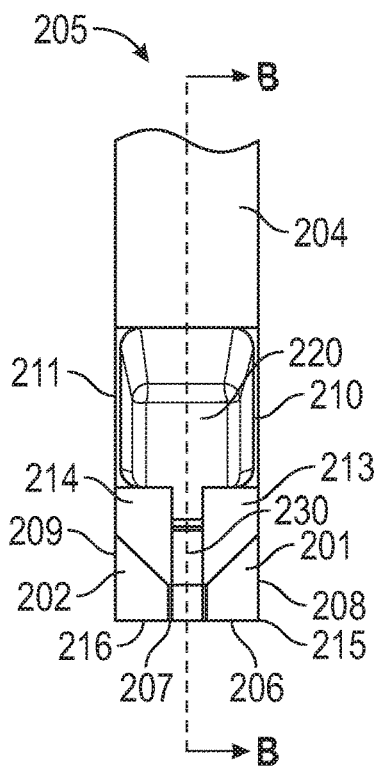
FIG. 15 shows a front view of the device of FIG. 14.
Figure 16:
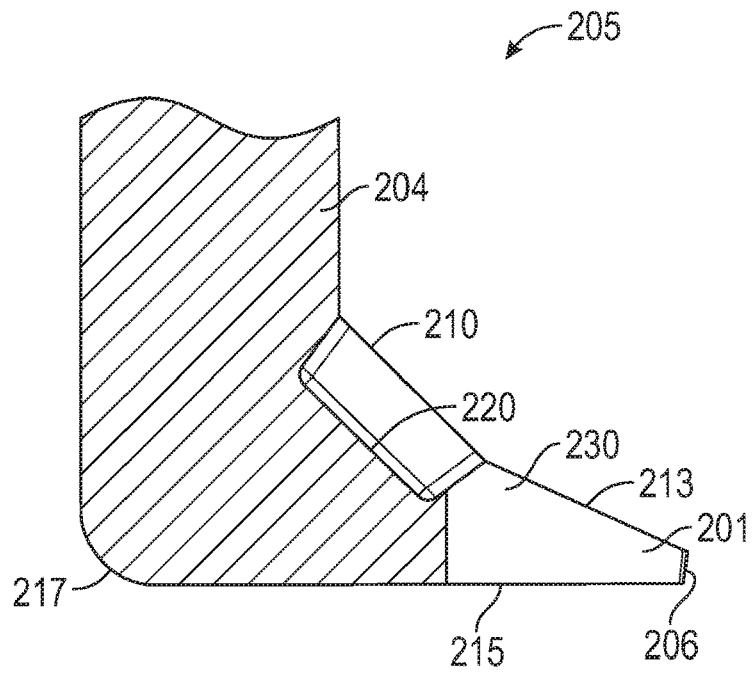
FIG. 16 shows a sectional side view of the device of FIG. 14.

Referring now to FIGS. 14-16, a device having a platform 205 can include some features similar to those of the device 12 illustrated in other figures. As shown in FIG. 14, a platform 205 of the device can extend from a shaft 204 and include first and second tips 206 and 207 at a distal side of the platform 205 and first and second top surfaces 213 and 214 of first and second platform portions 201 and 202, respectively, extending from the distal side of the platform 205 to a proximal side of the platform 205, opposite the distal side of the platform 205. The top surface 213 of the first platform portion 201 can extend from the first tip 206 to a first lateral element 210, and the top surface 214 of the second platform portion 202 can extend from the second tip 207 to a second lateral element 211.

The first and second platform portions 201 and 202 extend along the length of the platform 205 at least partially separated by a gap 230. For example, the gap 230 can extend proximally from the first and second tips 206 and 207 at least to the gap 220 between the lateral elements 210 and 211. Along at least a portion of the gap 230, the platform 205 can provide an entire height that is unoccupied. The width of the gap 230 along the length (e.g., Y-axis) of the platform 205 can be constant, variable, tapering along the length, or another shape. For example, the width can vary (e.g., taper) along the length between the proximal and distal ends of the platform 205, so that the gap 230 has a different width at proximal and distal sides thereof. The width of the gap 230 along the height (e.g., Z-axis) of the platform 205 can be constant, variable, tapering along the height, or another shape. For example, the width can vary (e.g., taper) along the height between the top and bottom surfaces of the platform 205, so that the gap 230 has a different width at top and bottom sides thereof. In the depicted example, inner walls of the first and second platform portions 201 and 202 defining the width of the gap 230 are substantially parallel to each other and/or nearby proximal portions of the opposing sides 208 and 209.

The gap 230 can intersect the gap 220. For example, the gap 220 can extend continuously to provide a space on a proximal side thereof that adjoins a distal side of the gap 220. The width of the gap 230 can be smaller than a width of the gap 220. While a proximal end of the gap 230 is depicted in FIG. 16 as terminating in a vertical wall, it will be understood that other structures and shapes are contemplated. For example, the platform 205 can provide a surface at a proximal end of the gap 230 that faces downward and/or a surface at a proximal end of the gap 230 that faces upward. Additionally or alternatively, the gap 230 can extend along the bottom of the platform toward or to the posterior end 217 (e.g., under the gap 220 and the lateral elements 210 and 211).

As shown in FIGS. 14 and 15, opposing sides 208 and 209 of the platform 205 can extend downwardly from the first and second top surfaces 213 and 214, respectively. The opposing sides 208 and 209 can be planar and/or parallel to each other. The first top surface 213 can transition to the first side 208 with a transition feature, and the second top surface 214 can transition to the second side 209 with a transition feature. While a sharp transition is shown in FIGS. 14 and 15, the transition features can have one or more other shapes, including bevel, curved, round, chamfer, fillet, etc.

As shown in FIGS. 14 and 15, opposing sides 208 and 209 of the platform 205 can extend downwardly from the first and second bottom surfaces 215 and 216, respectively. The first bottom surface 215 can transition to the first side 208 with a transition feature, and the second bottom surface 216 can transition to the second side 209 with a transition feature. While a sharp transition is shown in FIGS. 14 and 15, the transition features can have one or more other shapes, including bevel, curved, round, chamfer, fillet, etc.

The platform 205 can include the first and second bottom surfaces 215 and 216 extending from the first and second tip 206 and 207, respectively, at the distal side of the platform 205 to a posterior end 217 of the platform 205, opposite the tip 206. The first and second bottom surfaces 215 and 216 of the platform 205 can be positioned opposite the first and second top surfaces 213 and 214, respectively. The first and second bottom surfaces 215 and 216 can be configured to abut the outer wall of the Schlemm's canal during a procedure (see FIGS. 7-10). At least a portion of the first and second bottom surfaces 215 and 216 can be flat and/or planar. Additionally or alternatively, the first and second bottom surfaces 215 and 216 can be planar, convex, concave, or combinations thereof. The posterior end 217 can define a curved or round surface that transitions from the first and second bottom surfaces 215 and 216 to a portion of the shaft 204.

Trabecular meshwork received over the first and second top surfaces 213 and 214 is permitted to drop downward somewhat into the gap 230 between the first and second platform portions 201 and 202. The first and second top surfaces 213 and 214 can support elevation of trabecular meshwork without cutting thereon. For example, the first and second top surfaces 213 and 214 can include segments that each have a width greater than a width of the lateral elements 210 and 211. As the trabecular meshwork is stretched over first and second top surfaces 213 and 214, it can remain intact while brought to the lateral elements 210 and 211. Additionally, as the trabecular meshwork is stretched over the first and second top surfaces 213 and 214, it will be further stretched over the gap 230, which will provide a space between the first and second platform portions 201 and 202. The gap 230 can guide portions of the trabecular meshwork toward the gap 220 between the lateral elements 210 and 211. Platform portions 201 and 202 may be fixed relative to platform 205. Platform portions 201 and 202 may be moveable relative to platform 205. For example, platform portions 201 and 202 may function or act like tweezers for grasping portions of the trabecular meshwork disposed within the gap 230.

Conditions that might benefit from use of one or more of the devices disclosed herein include:

1. Primary open angle glaucoma
2. Normal or Low tension glaucoma
3. Pseudoexfoliation glaucoma
4. Pigment dispersion glaucoma
5. Angle closure glaucoma (acute, subacute, chronic)
6. Neo vascular or inflammatory glaucoma
7. Ocular hypertension
8. Other types of glaucoma that are related to high intraocular pressure The device could be used for research purposes to harvest TM or other small sheath of tissue for lab based studies or to harvest cells for in vitro culture needs. The device can be used to cut Anterior Synechiae or other cellular or fibrovascular membranes over the drainage angle such as those seen with ICE syndrome or neovascular glaucoma.

It is not intended that embodiments of the present disclosure be limited to any particular method, medical target, or device confirmation; however, it is believed that the device may be optimally designed to remove trabecular meshwork of the eye, unroofing small vessels (such as veins, arteries, lymphatic vessels, or other vessel with a lumen), and for creating a hole or opening in the tympanic membrane of the ear. It is not intended that embodiments of the present disclosure be limited to any particular mechanism; however, it is believed that creating an opening in the tympanic membrane of the ear may help aid in treating ear disease.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. An ophthalmic device comprising:
 a tool shaft;

a platform connected to the tool shaft, wherein the platform comprises:
an insertion tip on a distal end of the platform;
a bottom surface;
a first wall;
a second wall, wherein the first wall and the second wall intersect at the insertion tip;
a recessed portion defining a first unoccupied space between the first wall and the second wall;
a first lateral blade extending from the first wall and connecting the first wall to the tool shaft; and
a second lateral blade extending from the second wall and connecting the second wall to the tool shaft, the first lateral blade and the second lateral blade separated by a second unoccupied space,
wherein top surfaces of the first and second walls are parallel to a surface of the recessed portion.

2. The ophthalmic device of claim 1, wherein the first wall and the second wall each have a width that is greater than a width of the first lateral blade and the second lateral blade.

3. The ophthalmic device of claim 1, wherein the first wall and the second wall define a continuous planar surface.

4. The ophthalmic device of claim 1, wherein:
first heights of the platform between the bottom surface and the first wall increase as the platform extends proximally from the insertion tip;
second heights of the platform between the bottom surface and the second wall increase as the platform extends proximally from the insertion tip; and
third heights of the platform between the bottom surface and the recessed portion increase as the platform extends proximally away from the insertion tip.

5. The ophthalmic device of claim 4, wherein an average of the first heights and an average of the second heights is larger than an average of the third heights.

6. The ophthalmic device of claim 1, wherein a height of the platform between a distal end of the recessed portion and the bottom surface is smaller than a height of the platform between a point of intersection between the first wall and the second wall.

7. The ophthalmic device of claim 1, wherein the first and second lateral blades form an angle with respect to the bottom surface that is greater than an angle formed by the first wall, the second wall, and the recessed portion with respect to the bottom surface.

8. The ophthalmic device of claim 1, wherein proximal portions of the first and second walls are parallel to each other and distal portions of the first and second wall intersect at the insertion tip.

9. The ophthalmic device of claim 1, wherein the recessed portion has a constant width in a proximal section thereof and a tapered width in a distal section thereof.

10. An ophthalmic device comprising:
a tool shaft;
a single platform connected to the tool shaft, wherein the single platform comprises:
a solid single posterior end;
a first platform portion;
a second platform portion, the first platform portion and the second platform portion separated by a first unoccupied space, wherein the first platform portion, the second platform portion and the first unoccupied space are extending from the solid single posterior end to a front end of the single platform;
a first lateral blade extending from the first platform portion and connecting the first platform portion to the tool shaft; and a second lateral blade extending from the second platform portion and connecting the second platform portion to the tool shaft, the first lateral blade and the second lateral blade separated by a second unoccupied space.

11. The ophthalmic device of claim 10, wherein a width of the first unoccupied space is less than a width of the second unoccupied space.

12. The ophthalmic device of claim 10, wherein the first platform portion and the second platform portion each have a width that is greater than a width of each of the first lateral blade and the second lateral blade.

13. The ophthalmic device of claim 10, wherein:
the first platform portion increases in height as the first platform portion extends proximally from a first insertion tip; and
the second platform portion increases in height as the second platform portion extends proximally from a second insertion tip.

14. The ophthalmic device of claim 10, wherein the first platform portion and the second platform portion are laterally separated between entire heights thereof.

15. The ophthalmic device of claim 10, wherein the first and second lateral blades form an angle with respect to a bottom surface of the single platform that is greater than an angle formed by the first platform portion and the second platform portion with respect to the bottom surface.

16. The ophthalmic device of claim 10, wherein outer sides of the first platform portion and the second platform portion are parallel to each other at proximal segments thereof, and the outer sides are not parallel to each other at distal segments of the first platform portion and the second platform portion.

17. The ophthalmic device of claim 10, wherein inner sides of the first platform portion and the second platform portion are parallel to each other across the first unoccupied space.

18. The ophthalmic device of claim 10, wherein a width across the tool shaft, the first and second lateral blades, and a portion of the first and second platform portions is constant.

19. The ophthalmic device of claim 10, wherein a depth of the first unoccupied space is less than a depth of the second unoccupied space.

20. An ophthalmic device comprising:
a tool shaft;
a platform connected to the tool shaft, wherein the platform comprises:
an insertion tip on a distal end of the platform;
a bottom surface;
a first wall;
a second wall, wherein the first wall and the second wall intersect at the insertion tip;
a recessed portion defining a first unoccupied space between the first wall and the second wall;
a first lateral blade extending from the first wall and connecting the first wall to the tool shaft; and
a second lateral blade extending from the second wall and connecting the second wall to the tool shaft, the first lateral blade and the second lateral blade separated by a second unoccupied space,
wherein the recessed portion has a constant width in a proximal section thereof and a tapered width in a distal section thereof.

* * * * *